(12) United States Patent
Gordon (10) Patent No.: US 11,957,589 B2
(45) Date of Patent: Apr. 16, 2024

(54) NON-PATIENT-SPECIFIC CRANIOFACIAL IMPLANTS FOR CORRECTING AND/OR PREVENTING TEMPORAL OR PTERIONAL DEFORMITIES

(71) Applicant: Acumed LLC, Hillsboro, OR (US)

(72) Inventor: Chad Gordon, Cockeysville, MD (US)

(73) Assignee: Acumed LLC, Hillsboro, OR (US)

( * ) Notice: Subject to any disclaimer, the term of this patent is extended or adjusted under 35 U.S.C. 154(b) by 41 days.

(21) Appl. No.: 17/895,585

(22) Filed: Aug. 25, 2022

(65) Prior Publication Data

US 2023/0067769 A1 Mar. 2, 2023

Related U.S. Application Data

(60) Provisional application No. 63/237,703, filed on Aug. 27, 2021.

(51) Int. Cl.
*A61F 2/30* (2006.01)
*A61F 2/28* (2006.01)

(52) U.S. Cl.
CPC ............ *A61F 2/3094* (2013.01); *A61F 2/28* (2013.01); *A61F 2002/3092* (2013.01)

(58) Field of Classification Search
None
See application file for complete search history.

(56) References Cited

U.S. PATENT DOCUMENTS

| | | | |
|---|---|---|---|
| 9,549,819 B1 * | 1/2017 | Bravo | A61B 17/74 |
| 2003/0178387 A1 | 9/2003 | Amrich | |
| 2014/0364961 A1 * | 12/2014 | Mikhail | A61B 10/02 |
| | | | 623/23.52 |
| 2015/0045897 A1 | 2/2015 | Gordon et al. | |
| 2018/0116802 A1 * | 5/2018 | Daniel | A61B 17/8085 |
| 2018/0360610 A1 | 12/2018 | Patel et al. | |
| 2019/0021862 A1 * | 1/2019 | Kalpakci | A61F 2/30907 |
| 2019/0269817 A1 | 9/2019 | Williams et al. | |
| 2021/0106428 A1 | 4/2021 | Mahfouz | |

FOREIGN PATENT DOCUMENTS

| | | | |
|---|---|---|---|
| CN | 106236326 A | * | 12/2016 |
| ES | 2283108 T3 | | 10/2007 |
| RU | 2748678 C2 | | 9/2003 |
| RU | 2362493 C1 | | 7/2009 |

OTHER PUBLICATIONS

International Search Report corresponding to related International Patent Application No. PCT/US2022/041501 dated Dec. 30, 2022, 4 pages.
International Written Opinion corresponding to related International Patent Application No. PCT/US2022/041501 dated Dec. 30, 2022, 6 pages.

* cited by examiner

*Primary Examiner* — Javier G Blanco
(74) *Attorney, Agent, or Firm* — K&L Gates LLP (57) ABSTRACT

A non-patient specific implant for neuroplastic surgery is provided. The non-patient specific implant includes a three-dimensional mesh. The three-dimensional mesh comprises titanium. The three-dimensional mesh is pre-folded. The three-dimensional mesh is configured to replace a space for a hard tissue and/or a space for a soft tissue. The three-dimensional mesh has a three-dimensional triangular shape.

8 Claims, 5 Drawing Sheets

FIG. 5

NON-PATIENT-SPECIFIC CRANIOFACIAL IMPLANTS FOR CORRECTING AND/OR PREVENTING TEMPORAL OR PTERIONAL DEFORMITIES

PRIORITY CLAIM

The present application claims priority to and the benefit of U.S. Provisional Patent Application No. 63/237,703, filed on Aug. 27, 2021, the entirety of which is incorporated herein by reference.

BACKGROUND

The act of brain surgery may require a craniotomy of significant size. The majority (approximately 75%) of all craniotomies may be done within the perianal or temporal region. Thus, the temporal anatomy may become distorted due to devascularization and deinnervation of the critical structures such as the temporalis muscle and temporal fat pad (i.e., pertinent soft tissue). As such, facial symmetry may be forever jeopardized and distorted following the breach of this anatomy. In addition, a significant number of neurosurgical patients may lose the bone flap (i.e., the segment of bone removed for access to the brain) due to either infection, tumor involvement, brain swelling, and/or traumatic fracture. Therefore, there can be a deformity related to isolated soft tissue loss or a deformity related to combined hard and soft tissue low. Either way, a second surgery may be required, known as cranioplasty, to reconstruct the missing cranial bone and/or missing soft tissue bulk.

SUMMARY

Aspects of the present disclosure may relate generally to the field of reconstructive surgery, particularly cranioplasty, neuroplastic surgery, craniomaxillofacial surgery, and neurosurgery, and specifically to the field of improving form and function of non-customized implants for anatomical replacement. In an example, a non-patient specific implant for neuroplastic surgery may be provided. The non-patient specific implant may include a three-dimensional mesh. The three-dimensional mesh may include titanium. The three-dimensional mesh may be pre-folded.

In some examples of the present disclosure, which may be used in combination with any other example or combination of examples listed herein, the three-dimensional mesh may replace both of a space for a hard tissue and a space for a soft tissue.

In some examples of the present disclosure, which may be used in combination with any other example or combination of examples listed herein, the hard tissue may be a cranial bone and the soft tissue may be muscle and/or fat overlying the cranial bone.

In some examples of the present disclosure, which may be used in combination with any other example or combination of examples listed herein, the three-dimensional mesh may replace only a space for a soft tissue.

In some examples of the present disclosure, which may be used in combination with any other example or combination of examples listed herein, the soft tissue may be muscle and/or fat overlying a spinal bone.

In some examples of the present disclosure, which may be used in combination with any other example or combination of examples listed herein, the three-dimensional mesh may have a three-dimensional triangular shape.

In some examples of the present disclosure, which may be used in combination with any other example or combination of examples listed herein, the three-dimensional mesh may include a filling space with a predetermined volume. The filling space may be formed within three side edges and a curved central portion of the three-dimensional mesh.

In some examples of the present disclosure, which may be used in combination with any other example or combination of examples listed herein, the filling space may be configured to fill a volume of space for a hard tissue and/or a soft tissue to be replaced with the three-dimensional mesh.

In some examples of the present disclosure, which may be used in combination with any other example or combination of examples listed herein, a size of the three-dimensional mesh is in a range of about 5 cm to about 10 cm.

In some examples of the present disclosure, which may be used in combination with any other example or combination of examples listed herein, a size of the three-dimensional mesh is in a range of about 10 cm to about 15 cm.

In some examples of the present disclosure, which may be used in combination with any other example or combination of examples listed herein, a size of the three-dimensional mesh is in a range of about 15 cm to about 20 cm.

In some examples of the present disclosure, which may be used in combination with any other example or combination of examples listed herein, the three-dimensional mesh may be more rigid than porous polyethylene and silicone.

In some examples of the present disclosure, which may be used in combination with any other example or combination of examples listed herein, the three-dimensional mesh may be configured to be placed in a temporal fossa area.

In some examples of the present disclosure, which may be used in combination with any other example or combination of examples listed herein, the three-dimensional mesh may include one or more holes configured to receive a fastener.

In some examples of the present disclosure, a non-patient specific implant may include a three-dimensional titanium mesh. The three-dimensional titanium mesh may be pre-folded and the three-dimensional titanium mesh may have a three-dimensional triangular shape.

Additional features and advantages of the disclosed apparatus or systems are described in, and will be apparent from, the following Detailed Description and the Figures.

DETAILED DESCRIPTION OF EXAMPLE EMBODIMENTS

Aspects of the present disclosure are disclosed in the following description and the related drawings. Those skilled in the art will recognize that alternate embodiments may be devised without departing from the spirit or the scope of the claims. Additionally, well-known elements of exemplary embodiments of the present disclosure may not be described in detail or may be omitted so as not to obscure the relevant details of the present disclosure.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage, or mode of operation.

The present disclosure may refer to technologies developed by the present inventor to capitalize on craniofacial implants for correcting and/or preventing temporal and pterional-style hollowing deformities commonly encountered in neurosurgical patients, the disclosure of which is incorporated herein in its entirety.

Man-made implants may be designed for anatomical replacement with respect to the bone (e.g., hard tissue) defects which they replace. They may be pre-designed using computer-assisted design/manufacturing (CAD/CAM) as customized, patient-specific implants, or can be pre-designed using anatomical averaging as "off-the-shelf", one-size-fits-all implants. Either way, both implant manufacturing processes equate to a pre-fabricated implant manufactured from a safe, biocompatible, alloplastic material which holds its shape and form with respect to time. Examples of the alloplastic material used for such implants may include porous polyethylene or silicone.

In some examples, a customized solution for correcting and/or preventing temporal hollowing deformities may be provided. Some such solutions may replace both missing bone and soft tissue in the craniofacial region and are disclosed in U.S. Pat. No. 10,639,158, titled PATIENT-SPECIFIC CRANIOFACIAL IMPLANTS, filed Apr. 8, 2019, the disclosure of which is hereby incorporated by reference in its entirety. However, in some cases, there may be a need for a non-patient specific craniofacial implants for correcting and/or preventing temporal or pterional deformities given the pre-operative time, labor and expense needed to design a customized, "one-and-only" shape solution for each patient in need.

Alloplastic implants sold commonly as "universal" solutions, for correcting or preventing temporal deformity 13 such as the commonly employed, off-the-shelf, non-customized pterional implant made of porous polyethylene (i.e., MedPor) or silicone—may be suboptimal given that it has a much higher propensity to post-operative infection risk and a lower surgeon preference or comfortability.

Bony anatomies constructing certain aspects of the human body may maintain a constant form and, thus, lend themselves well to the field of implantable implants in that their shape and form may stay ever-constant. Conversely, soft tissue areas found over the bone, such as with muscle and fat, may be constantly changing in shape depending on one's bodily movements throughout the day, and therefore have inconsistent boundaries challenging the task of implant design. Thus, a solution taking into account these factors would be desirable.

For example, during neurosurgical procedures, diseased or damaged portions of the head (post-craniotomy or craniectomy defects) may be safely reconstructed and replaced, using a craniofacial implant to replace atrophic temporal fat pad bulk, temporalis muscle bulk, and/or temporal bone—all of which are commonly affected by way of the standard pterional-style craniotomy. Following temporary removal or permanent resection of this pterional-area cranial bone for the purpose of neurosurgery or craniofacial plastic surgery, such defects are often reconstructed with either custom craniofacial implants (CCIs) or "off-the-shelf", non-patient specific implants most commonly made of porous polyethylene.

Recent modifications by the present inventor have revolutionized the field of soft tissue replacement surgery and is termed "temporal hollowing or temporal deformity correction"—by which a clinician, such as a neuroplastic surgeon or neurosurgeon, manually installs/reshapes/resizes either a previously-ordered, custom implant or "off-the-shelf" plastic implant to fit perfectly into the temporal fossa defect as true anatomical replacement. Either way, for these methods involving cranioplasty reconstruction for pre-defined temporal or pterional defects, the advent of computer-aided design/manufacturing (CAD/CAM), has provided surgeons with perfectly-shaped implants designed and manufactured based in part on fine cut preoperative computed tomography (CT) scans and three-dimensional reconstruction (+/−stereolithographic models). However, present day challenges limit themselves to the fact that the most popular "off-the-shelf" solution used for non-patient specific reconstruction are made out of a suboptimal alloplastics known as porous polyethylene (i.e., MedPor) or silicone; by way of human anatomical averaging; a common design method employed to eliminate the accompanying cost, pre-operative time allotment and labor needed to fabricate and design the alternative option, being a "patient-specific" implant.

Aspects of the present disclosure may address the issues in the related art by providing a titanium mesh with a three-dimensional bending shape consistent with a triangular shape in various sizes (extra-small, small, medium, large and extra-large), capable of replacing one or both of hard tissue (e.g., bone) and soft tissue (e.g., overlying muscle and fat). The titanium mesh according to the present disclosure may be a more dependable material in the fight against post-operative infection and improve intraoperative handling to truly advance the field.

The titanium mesh according to the present disclosure may be more resistant to external forces related to incidental head trauma than alloplastic materials. Aspects of the present disclosure may advance the field by pre-fabricating soft and/or hard tissue implants with folded titanium mesh, which may provide the ultimate, "off-the-shelf", non-custom solution unlike ever before. Thus, the field of soft and hard tissue replacement for neuroplastic surgery, neurosurgery and craniofacial surgery would greatly be improved by changing both the material and the shape to include titanium mesh (with or without a special coating or polishing), to provide surgeons a much improved solution towards the fight against preventing and/or correcting temporal and pterional deformities following neurosurgery.

The use of CCIs designed with dual-purpose may be able to preserve post-neurosurgery appearance, prevent post-operative deformity with accompanying social stigma, decrease total operative times, prevent scalp-related wound complications and enhance patient satisfaction. This major advance can be accomplished by using a novel design algorithm provided by the present inventor which capitalized on the under-utilized hard and soft tissue space around the brain (thereby erasing the old, outdated, generational dogma that cranial implants could be designed for the anatomical bone space) and using pre-operative, CAD/CAM design. However, at the time, this solution requires the employment of an alloplastic material like porous polyethylene (MedPor), polymethyl methacrylate (PMMA), or PEEK—which can be laser-sintered and/or molded to a customized shape. Previously, it was not known or understood that a two-dimensional piece of titanium mesh, could be pre-folded back on itself—quite similar to the art of origami. Aspects of the present disclosure may provide a pre-folded titanium mesh, which may remove all of the extra cost and labor needed to make each implant "customized".

Figure 1:
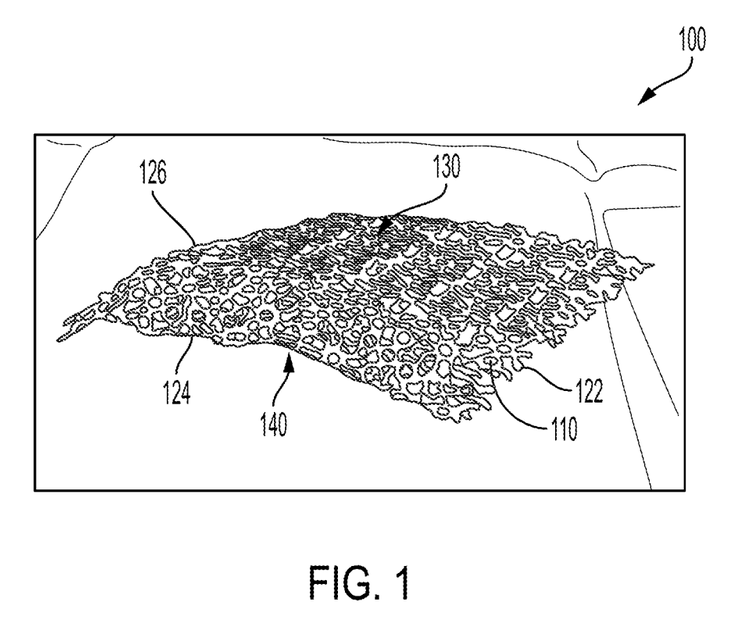
FIG. 1 shows an exemplary embodiment of a non-patient-specific implant for correcting and/or preventing temporal or pterional deformities.

FIG. 1 illustrates an example non-patient specific implant 100 according to the present disclosure. In some examples, the non-patient specific implant 100 may be made of titanium mesh. The non-patient specific implant 100 may be pre-fabricated using anatomical averaging. The non-patient specific implant 100 may have various sizes, for example, extra-small, small, medium, large and extra-large. The non-patient specific implant 100 may be pre-folded in a way to accommodate various degrees of pre-existing soft tissue atrophy. For example, each of the non-patient specific titanium mesh implants in various sizes may have a varying amount of volume, for example, inside the triangular-shaped implant. In some examples, the side edges of the titanium mesh may be pre-folded back.

In some examples, the non-patient specific implant 100 may include various other features. For example, the non-patient specific implant 100 may include one or more holes 110. The one or more holes 110 may be configured to receive a fastener. Examples of the fastener may include a screw, a nail, and a bolt. The one or more holes 110 in the non-patient specific titanium mesh implant 100 may facilitate the fixation of the fastener (e.g., easier to fixate to the human craniofacial skeleton), which may save the surgeon time and effort, and provide many more usable options for the surgeons to place the fastener through for the purpose of permanent fixation—as opposed to the less rigid porous polyethylene or silicone implants—which may require more complex methods for skull fixation. Again, one may need to be careful to minimize any micromotion of an anatomical implant after surgery, or else the foreign body may have an increased prevalence for infection and ultimate removal. Therefore, aspects of the present disclosure may provide a much improved characteristic versus a non-patient specific implant made of plastic (i.e., porous polyethylene).

Aspects of the present disclosure may provide the surgeon with an implant accompanying much improved rigidity and structural integrity to the missing bone and/or soft tissue—which is significantly lacking when it comes to plastic materials (i.e., porous polyethylene)—which more easily bend with external trauma. In some examples, the non-patient specific titanium mesh implant 100 according to the present disclosure may replace the missing volume of hard and soft tissue to correct and/or prevent visible contour deformity based on the volume maintained within the titanium mesh implant (e.g., within the triangular design).

In some examples, the non-patient specific titanium mesh implant 100 according to the present disclosure may fill in the neighboring spaces of the hard and/or soft tissue. For example, the non-patient specific titanium mesh implant according to the present disclosure can be used for isolated soft tissue replacement and/or in situations where both hard and soft tissues need replacement.

In some examples, the non-patient specific titanium mesh implant 100 according to the present disclosure can be used with other types of implants. For example, the non-patient specific titanium mesh implant 100 according to the present disclosure can be affixed to the outside of a pre-fabricated customized implant made of alloplastic material, including PEEK, porous polyethylene, and/or PMMA, which may not have a (pre-augmented) soft tissue area.

In some examples, the non-patient specific implant 100 may be provided for combined hard and soft tissue reconstruction with novel utilization of three-dimensional, origami-like, folded titanium mesh for improving form and function, an anatomic-specific implant for reconstructive surgery. In some examples, the non-patient specific implant 100 according to the present disclosure may go beyond a hard tissue replacement design using a flat, two-dimensional piece of titanium mesh for standard bone replacement. In some examples, the non-patient specific implant 100 according to the present disclosure may include a flat piece of titanium mesh being pre-folded in a unique triangular fashion based on anatomical averaging for combined soft tissue and hard tissue reconstruction, for example, by way of pre-fabricating five different sizes for off-the-shelf availability including extra-small, small, medium, large and extra-large. The varying space/footprint may relate to the volume of space incorporated within the center of the folded, origami-like, triangular titanium mesh implant.

In some examples, the non-patient specific implant 100 according to the present disclosure may include titanium mesh that may replace the cranial bone and/or overlying soft tissue space. This may provide the reconstructive field an improved alternative versus the less-desirable, commonly-used implant made of porous polyethylene or silicone.

In some examples, the non-patient specific implant 100 according to the present disclosure may employ the titanium mesh in a way that is folded similar to origami. This may replace the less-desirable infection risk commonly associated with alloplastic materials like porous polyethylene. In some examples, the non-patient specific implant according to the present disclosure may have a three-dimensional triangular shape as shown in FIGS. 1 to 5 and may have a ranging spectrum of profile width (narrow>>>wide), which may represent the internal volume space on the inside matching to the severity of missing soft tissue atrophy or expected changes post-neurosurgery.

For example, the non-patient specific implant 100 may have three side edges (first side edge 122, second side edge 124, third side edge 126) connected to each other, and the three side edges 122, 124, 126 may define the boundaries of the non-patient specific implant 100. The central portion 130 of the non-patient specific implant 100 may be curved. For example, the central portion 130 of the non-patient specific implant 100 may have a convex curve, forming a filling space 140 with a predetermined volume within the three side edges 122, 124, 126 and the curved central portion 130. In some examples, the filling space 140 may correspond to a volume of space for a hard tissue and/or a soft tissue to be replaced with the three-dimensional mesh.

Aspects of the present disclosure may be used for additional muscle and fat volume overlying critical areas around the brain/skull. In some examples, aspects of the present disclosure may provide a rigid non-patient specific implant made of pre-folded titanium mesh, which may allow it to safely replace various tissue types, including bone, muscle and/or fat. The soft tissue implant may include embedded neurotechnologies of various function that may provide life-enhancing, life-changing and/or life-saving modalities to the nearby brain, for example, since there might be unutilized space within the triangular titanium mesh implant. The soft tissue implant component inside the folded titanium mesh may be interchangeable with another soft tissue implant component in plug-and-play fashion (if and/or when the previous technology is no longer needed).

Some descriptions related to patient-specific craniofacial implants are disclosed in U.S. Pat. No. 10,639,158, titled PATIENT-SPECIFIC CRANIOFACIAL IMPLANTS, filed Apr. 8, 2019, the disclosure of which is hereby incorporated by reference in its entirety, which describe the replacement of the missing soft tissue at the same time of skull reconstruction, by employing computer-assisted design algorithms concentrating on the above soft tissue. Further innovations may include an improved design that may involve better-defined anatomical vector lines for improved consistency (i.e., enhanced results), a pre-fabricated temporal window to prevent soft tissue impingement at time of placement and placing these craniofacial implants above the scarred-down temporalis muscle as opposed to underneath it. However, these "dual-purpose craniofacial implants" (e.g., the first purpose is to replace missing bone for brain protection and the second purpose is to restore facial symmetry secondary to soft tissue deformity) may be made and delivered using an alloplastic material (i.e., porous polyethylene, PMMA, and PEEK), as disclosed in Zhong et al., "Quantitative Analysis of Dual-Purpose, Patient-Specific Craniofacial Implants for Correction of Corporal Deformity", the disclosure of which is incorporated herein in its entirety. However, as discussed above, the alloplastic material may be an inferior solution for temporal and pterional-style deformities given the bacterial infection risk and poor surgeon usability. Furthermore, there are times when the customized craniofacial implant is received for surgery and is missing the bulked out first described by the present inventor. In contrast, the non-patient specific titanium mesh implant according to the present disclosure may have a much improved profile with respect to both surgeon familiarity, a more desirable user profile, and a much more optimal infection-resistant profile. Hence, it can be employed by itself, as well as placed on the outside of "bone-only" replacement craniofacial implant inadequately prepared to correct and/or prevent temporal hollowing.

Figure 2:
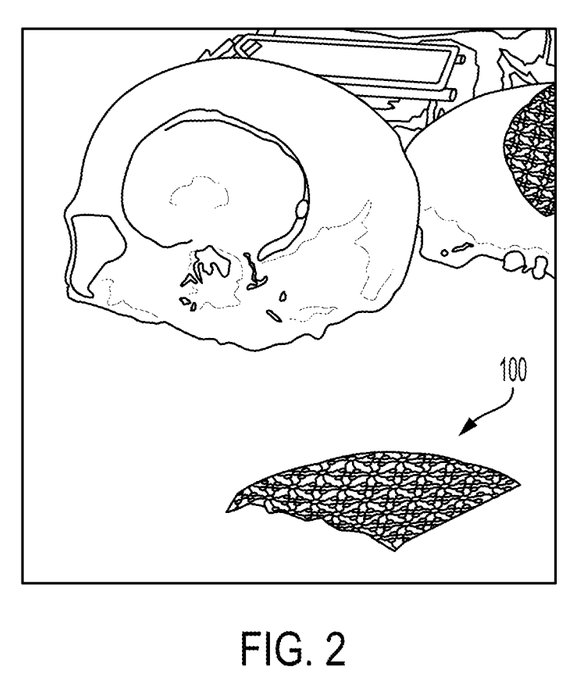
FIG. 2 shows an exemplary embodiment of a non-patient-specific implant for correcting and/or preventing temporal or pterional deformities.
Figure 3:
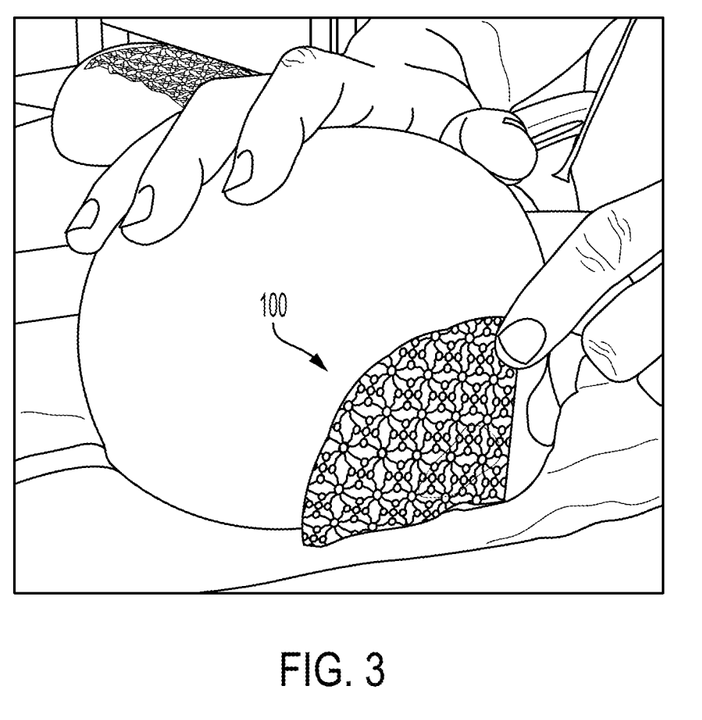
FIG. 3 shows an exemplary embodiment of a non-patient-specific implant for correcting and/or preventing temporal or pterional deformities.
Figure 4:
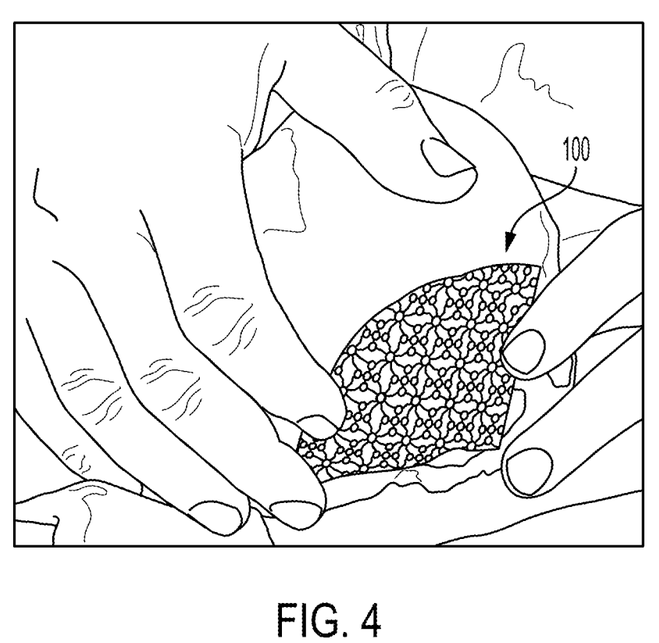
FIG. 4 shows an exemplary embodiment of a non-patient-specific implant for correcting and/or preventing temporal or pterional deformities.
Figure 5:
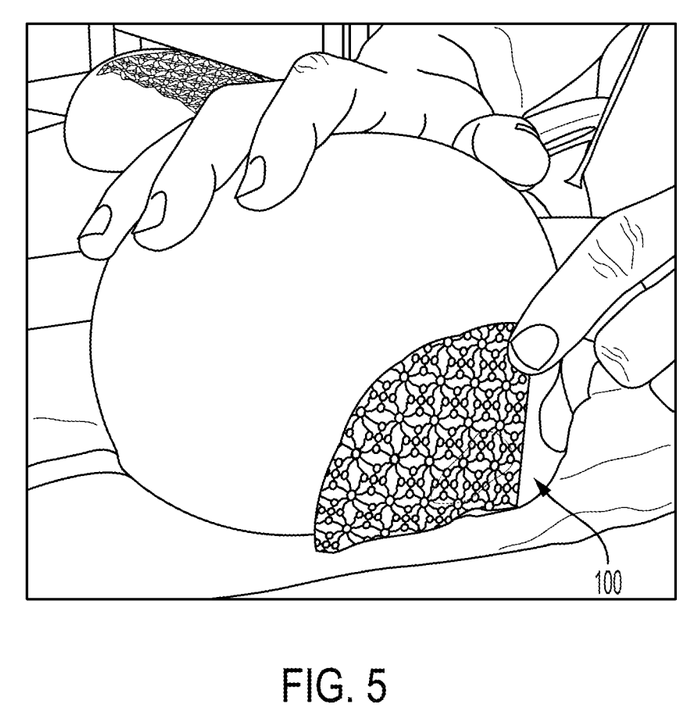
FIG. 5 shows an exemplary embodiment of a non-patient-specific implant for correcting and/or preventing temporal or pterional deformities.

As shown in the figures, aspects of the present disclosure may provide a unique, origami-like, three-dimensional folded titanium mesh implant (see FIGS. 1 and 2). In some examples, the non-patient specific titanium mesh implant according to the present disclosure may be attached to the outside of a standard cranial bone flap or replacement implant (see FIGS. 3 to 5). The implant can be formed with an extra-small-, small-, medium-, large- or extra-large-sized implant design—which the surgeon can decide to use at time of cranioplasty based on intraoperative assessment and degree of soft tissue resorption.

In some examples, the non-patient-specific implant 100 according to the present disclosure can be delivered as an "off-the-shelf" implant following virtual shape creation by way of human anatomical averaging and CAD/CAM design, for example, including: a) a craniofacial implant designed to replace missing cranial bone (i.e., pre-existing skull defect); and b) soft tissue designed to replace missing temporalis muscle/fat wherein the fabrication process provides enough internal volume (e.g., within the filling space 140). The internal space component (e.g., filling space 140) may be delivered in extra-small, small-, medium-, large- or extra-large sized dimensions to accommodate different degrees of expected soft tissue resorption following neurosurgery or pre-existing deformity, thus the pre-formed sizes can vary in terms of length, width and height. An exemplary clinical scenario for such embodiments may be one where patients with pre-existing skull defects require neuroplastic surgery and/or pre-existing soft tissue defects after neurosurgery.

In some examples, an improved implant may offer the surgeon a "non-patient-specific craniofacial implant" for neurosurgical patients. In instances where neurotechnology becomes refined and with smaller footprints, these functional devices could be pre-designed to fill-in to the triangular area within the pre-folded titanium mesh implants sitting within the temporal fossa, since the space inside is void of anything.

In some examples, the non-patient-specific implant 100 according to the present disclosure may be delivered as one folded titanium mesh, origami-like implant following human anatomical averaging and CAD/CAM design including: a) a non-patient-specific, soft tissue implant designed to replace missing temporalis muscle/temporal fat pad/subcutaneous tissue, wherein the fabrication process provides numerous holes for fastener (e.g., screw) connection to the nearby surrounding healthy cranial bone at time of implantation. The soft tissue component may be delivered in extra-small, small-, medium-, large- or extra-large sized dimensions to accommodate different degrees of expected soft tissue resorption. An exemplary clinical scenario for such embodiments may be one where patients have pre-existing soft tissue defects following neurosurgical craniotomy defects requiring neuroplastic surgery.

In some examples, a non-patient-specific soft tissue implant for neurosurgical patients in anticipation of future deformity may be provided. As such, an extra-small, small-, medium-, large- and extra-large sized soft tissue implant component may be delivered to the surgeon in a pre-sterilized package—which the surgeon may decide based on intraoperative assessment and degree of soft tissue mobilization identified at time of craniotomy or in instances where the neurosurgeon knows post-operative irradiation is needed for cancer control and that a temporal/pterional soft tissue deformity is to be expected in the future.

In some examples, another indication for use of the novel dual-purpose implants as described hereinabove, would be in instances of planned craniectomy (i.e., elective removal of non-diseased or normal cranial bone). Many neurosurgical procedures are planned on brain disease that is covered by normal, healthy bone (for patients who have never had surgery in the targeted area and have undisrupted anatomy present). However, as the field of neuroplastic surgery continues to expand, the use of non-patient specific implants will become more commonly employed in all neurosurgical patients undergoing temporal and pterional-style craniotomies, as a way to combat any risk for post-neurosurgical deformity and the accompanying social stigma of having a craniofacial deformity. In other words, neurosurgical patients may desire the appearance of their pre-operative self (in addition to safe brain surgery), quite similar to the parallel revolution that started back in 1950's with breast cancer patients wanting to have reconstruction at the time of cancer removal. Hence, aspects of the present disclosure may offer the surgeon an origami-like, pre-folded titanium mesh implant design with a standard cranial bone replacement implant, along with an extra-small, small-, medium-, large- and extra-large sized soft tissue implant component—which the surgeon can decide to use at time of craniotomy based on intraoperative assessment and degree of soft tissue resorption.

In some examples, for patients in need of planned reconstruction by way of neuroplastic surgery, aspects of the present disclosure may provide an improved treatment strategy via neuroplastic surgery. As these three-dimensional, non-patient specific craniofacial implants become more refined with enhanced footprints, the non-patient specific implant according to the present disclosure could be pre-folded to fill-in soft tissue elements around the spinal cord, instead of needing to replace both spinal bone and spinal soft tissue for placement.

Aspects of the present disclosure may provide a method for providing the non-patient specific titanium mesh implant. In some examples, various sizes (e.g., three to five sizes) for the non-patient specific titanium mesh implant may be selected, for example, to cover the most common sizes of bony defect of void in such a manner as they provide the desired neuroplastic effect along with minimal overlap on the bone surrounding the bony defect and/or void. In some examples, the non-patient specific titanium mesh implant 100 according to the present disclosure may have a size (e.g., length/width) in a range of about 5 cm to about 10 cm, about 10 cm to about 15 cm, or about 15 cm to about 20 cm. In other examples, the non-patient specific titanium mesh implant 100 according to the present disclosure may have any other suitable size. In some examples, the non-patient specific titanium mesh implant according to the present disclosure may be formed and utilized in any of a variety of manners. In some examples, the non-patient specific titanium mesh implant according to the present disclosure may be 3D printed.

In some examples, the selected size of the non-patient specific titanium mesh implant 100 may be treated, cut, or otherwise formed in a suitable manner. For example, the non-patient specific titanium mesh implant may be molded, cut, and/or otherwise formed pre-operatively such that it can fill and resolve the existing skull defect while also preserving any desired craniofacial symmetry with non-defect areas.

In some examples, once the appropriately sized implant is chosen, any further modifications may be performed prior to the implant being surgically placed. In some examples, no further modification may be needed due to the selection of an appropriately sized implant (among the given size). In some examples, the non-patient specific titanium mesh implant according to the present disclosure may be sterilized (and provided in a pre-sterilized package).

In some examples, before or after cutting, the non-patient specific titanium mesh implant may be coated or polished. For example, a frictionless coating process may be applied to the non-patient specific titanium mesh implant according to the present disclosure to make it more smooth and suitable, for example, for the constantly moving, mobile scalp and soft tissue above for long-term durability, and therefore improving on the current "sandpaper-like" titanium mesh products currently on the market. In some examples, this coating and/or manufacturing/finishing process, which may decrease the abrasiveness of the titanium mesh may allow for effective gliding to occur and decrease risk for eventual extrusion, infection, removal and failure—particularly in instances over thin scalps from repeated surgery or irradiation therapy for tumor disease.

In some examples, the non-patient specific titanium mesh implant according to the present disclosure may be polished such that it is smooth or not otherwise coarse. Thus, the non-patient specific titanium mesh implant according to the present disclosure may perform in a desired and effective manner to protect the soft scalp and soft tissue (i.e., temporalis muscle and temporal fat pad) above the implant following implantation from long-term injury, eventual atrophy, and/or erosion leading to failure and removal.

In some examples, the titanium mesh craniofacial implant according to the present disclosure may be pre-bent prior to implantation. This can be desirable because there are typically no flat-shaped skull defects in a human given the cranium's radius of curvature. Thus, having titanium mesh implants supplied with a flat shape may only mandate additional effort and time in the operating room, which are undesirable from safety, time, and cost perspectives. The pre-bending of the titanium mesh craniofacial implant during the fabrication process can thereby reduce surgeon effort before and during surgery, reduce the amount of associated artistry involved in properly forming and modelling a craniofacial implant so as to achieve the desired remediation of the defect and preserve craniofacial symmetry using surgical know-how related to addressing contour irregularities associated with cranioplasty reconstruction, and, ultimately, result in an improved implant that has improved functionality in exposure-prone areas and also improved post-operation appearance on the recipients of the implant.

In some examples, the non-patient specific titanium mesh implant according to the present disclosure may include a countersink to allow a much lesser or shallower fastener (e.g., screw) profile during inset. In some examples, the one or more holes in the non-patient specific titanium mesh implant according to the present disclosure may serve as a countersink. With a typical screw for neuroplastic implants having a length of 4 mm, where 2 mm is inserted into bone and 2 mm is in the mesh or implant, the countersink can provide for a decrease of 1 mm or more. In other words, with the countersink, 3 mm of a 4 mm screw can be inserted into bone with only 1 mm in the mesh or implant. The result can provide a flat implant profile. Thus, the countersink along the mesh implant can improve outcomes with a smooth or smoother contour of the craniofacial implant since having flat-head screws inside countersunk areas may provide the ultimate low-profile construct. Small screw edges underneath a thin or atrophied scalp, particularly with smokers or radiated patients, can be quite problematic and include symptoms such as chronic pain, visible deformity, and may even lead to extrusion/infection necessitating the removal of mesh implant, all of which can be decreased with the countersink.

In some examples, the non-patient specific titanium mesh implant according to the present disclosure may be symmetrical. In other examples, the non-patient specific titanium mesh implant according to the present disclosure may be asymmetrical. The asymmetrical structure may provide for additional angles for bending and shaping the implant, leading to easier, less time consuming, and more accurate implant structures.

In some examples, the non-patient specific titanium mesh implant according to the present disclosure may be placed on top of the temporalis muscle in an effort to prevent disruption of neo-angiogenesis and unnecessary bleeding. Such placement of the titanium mesh craniofacial implant may provide for desired reconstruction of the temporal area as well as the missing bone in the skull defect, which is especially relevant in instances of secondary cranioplasty following head trauma or tumor requiring craniectomy and staged surgery to follow.

As used herein, "about," "approximately" and "substantially" are understood to refer to numbers in a range of numerals, for example the range of −10% to +10% of the referenced number, preferably −5% to +5% of the referenced number, more preferably −1% to +1% of the referenced number, most preferably-0.1% to +0.1% of the referenced number. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

Reference throughout the specification to "various aspects," "some aspects," "some examples," "other examples," "some cases," or "one aspect" means that a particular feature, structure, or characteristic described in connection with the aspect is included in at least one example. Thus, appearances of the phrases "in various aspects," "in some aspects," "certain embodiments," "some examples," "other examples," "certain other embodiments," "some cases," or "in one aspect" in places throughout the specification are not necessarily all referring to the same aspect. Furthermore, the particular features, structures, or characteristics illustrated or described in connection with one example may be combined, in whole or in part, with features, structures, or characteristics of one or more other aspects without limitation.

When the position relation between two parts is described using the terms such as "on," "above," "below," "under," and "next," one or more parts may be positioned between the two parts unless the terms are used with the term "immediately" or "directly." Similarly, as used herein, the terms "attachable," "attached," "connectable," "connected," or any similar terms may include directly or indirectly attachable, directly or indirectly attached, directly or indirectly connectable, and directly or indirectly connected.

It is to be understood that at least some of the figures and descriptions herein have been simplified to illustrate elements that are relevant for a clear understanding of the disclosure, while eliminating, for purposes of clarity, other elements. Those of ordinary skill in the art will recognize, however, that these and other elements may be desirable. However, because such elements are well known in the art, and because they do not facilitate a better understanding of the disclosure, a discussion of such elements is not provided herein.

The terminology used herein is intended to describe particular embodiments only and is not intended to be limiting of the present disclosure. As used herein, the singular forms "a," "an," and "the" are intended to include the plural forms as well, unless otherwise indicated. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "at least one of X or Y" or "at least one of X and Y" should be interpreted as X, or Y, or X and Y.

It should be appreciated that the embodiments disclosed herein may further be modified without departing from the spirit of the invention. Furthermore, in some examples, the non-patient specific implant according to the present disclosure may be constructed of any materials that enable them to function as described herein, for example various man-made biomaterials and/or 3-d printed titanium, or any combination thereof. Furthermore, in some examples, both a bone implant and the soft tissue implant may include cavities therein for embedded neurotechnologies, similar to the embodiments described above.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

The invention is claimed as follows:

1. A non-patient specific craniofacial implant for neuroplastic surgery, the non-patient specific implant comprising:
   a three-dimensional titanium mesh,
   wherein the three-dimensional titanium mesh is pre-folded,
   wherein the pre-folded three-dimensional titanium mesh has a three-dimensional triangular shape,
   wherein the three-dimensional titanium mesh includes a filling space with a predetermined volume, wherein the filling space is formed within three side edges and a curved central portion of the three-dimensional titanium mesh,
   wherein the filling space is sized and configured to fill a volume of space for a hard tissue of a cranial bone and/or a soft tissue of a cranial bone to be replaced with the three-dimensional titanium mesh.

2. The non-patient specific craniofacial implant of claim 1, wherein the soft tissue comprises muscle and/or fat overlying a cranial bone.

3. The non-patient specific craniofacial implant of claim 1, wherein a size of the three-dimensional titanium mesh is in a range of about 5 cm to about 10 cm.

4. The non-patient specific craniofacial implant of claim 1, wherein a size of the three-dimensional titanium mesh is in a range of about 10 cm to about 15 cm.

5. The non-patient specific craniofacial implant of claim 1, wherein a size of the three-dimensional titanium mesh is in a range of about 15 cm to about 20 cm.

6. The non-patient specific craniofacial implant of claim 1, wherein the three-dimensional titanium mesh is more rigid than porous polyethylene and silicone.

7. The non-patient specific craniofacial implant of claim 1, wherein the three-dimensional titanium mesh is configured to be placed in a temporal fossa area.

8. The non-patient specific craniofacial implant of claim 1, wherein the three-dimensional titanium mesh comprises one or more holes configured to receive a fastener.

* * * * *